(12) United States Patent
Zhang et al.

(10) Patent No.: US 12,360,092 B2
(45) Date of Patent: Jul. 15, 2025

(54) METHOD, DEVICE, AND STORAGE MEDIUM FOR MEASURING NITROGEN CONTENT

(71) Applicant: SHANGHAI LIFENGAS CO., LTD, Shanghai (CN)

(72) Inventors: Zhengxiong Zhang, Shanghai (CN); Kevin Ren, Shanghai (CN)

(73) Assignee: SHANGHAI LIFENGAS CO., LTD, Shanghai (CN)

( * ) Notice: Subject to any disclaimer, the term of this patent is extended or adjusted under 35 U.S.C. 154(b) by 0 days.

(21) Appl. No.: 18/764,362

(22) Filed: Jul. 4, 2024

(65) Prior Publication Data

US 2024/0385161 A1    Nov. 21, 2024

Related U.S. Application Data

(63) Continuation of application No. PCT/CN2024/093024, filed on May 14, 2024.

(30) Foreign Application Priority Data

May 15, 2023    (CN) .......................... 202310545731.3

(51) Int. Cl.
| | |
|---|---|
| *F25J 3/04* | (2006.01) |
| *G01N 33/00* | (2006.01) |
| *G06F 30/20* | (2020.01) |
| *G06N 20/00* | (2019.01) |

(52) U.S. Cl.
CPC ...... *G01N 33/0036* (2013.01); *F25J 3/04793* (2013.01); *G01N 33/0068* (2024.05); *G06F 30/20* (2020.01)

(58) Field of Classification Search
CPC .......... G01N 33/0036; G01N 33/0068; G01N 33/0062; G01N 33/225; G01N 33/004; G01N 33/0037; G06F 30/20; F25J 3/04793; G06N 20/00; G16C 20/70; G05B 17/02; G05B 13/027
USPC ...... 700/45, 31; 702/24, 19, 23, 181, 1, 179, 702/183
See application file for complete search history.

(56) References Cited

FOREIGN PATENT DOCUMENTS

| CN | 104697937 A | * | 6/2015 | |
|---|---|---|---|---|
| CN | 106525731 A | * | 3/2017 | ............. G01N 21/25 |
| CN | 109459392 B | * | 6/2019 | ............. A01G 22/22 |
| CN | 113724800 A | * | 11/2021 | |

* cited by examiner

*Primary Examiner* — Jeffrey P Aiello
(74) *Attorney, Agent, or Firm* — Ying-Ting Chen

(57) ABSTRACT

Disclosed are a method, a device, and a storage medium for measuring the nitrogen content. The method includes determining related variables associated with the nitrogen content; establishing an initial model, wherein the initial model takes the related variables as independent variables and the nitrogen content as dependent variables according to a historical operation data, and calculating parameters in the initial model; according to parameters in the initial model, obtaining parameters in a soft-sensing model by fitting; according to detected values of the related variables and the soft-sensing model, predicting the nitrogen content in real-time; and according to the predicted nitrogen content and an actual nitrogen content obtained by periodic sampling, obtaining a fusion detection result.

16 Claims, 2 Drawing Sheets

METHOD, DEVICE, AND STORAGE MEDIUM FOR MEASURING NITROGEN CONTENT

CROSS REFERENCE OF RELATED APPLICATION

This application is a Continuation Application of the International Application PCT/CN2024/093024, filed on May 14, 2024, which claims priority to Chinese Patent Application No. CN 202310545731.3, filed on May 15, 2023, the contents of which are incorporated herein by reference in its entirety.

TECHNICAL FIELD

The present disclosure relates to the technical field of air separation, in particular to a method, a device, and a storage medium for measuring nitrogen content.

BACKGROUND

Argon is an inert gas with stable chemical properties and is not easy to react with other substances. In industry, argon is widely used in metal welding, smelting and processing, semiconductor production, laser cutting, medical imaging, and other fields. Argon is important in these scenarios because it provides a protective, stable, and inert environment.

When the nitrogen content in the argon fraction of the air separation unit is too high and lasts for a long time, it will cause nitrogen blockage in the condenser of the crude argon column, destroy the distillation condition of the air separation unit, and affect the normal production of argon. Excessive higher nitrogen content in argon fraction will affect the stable operation of the plant. Excessive lower nitrogen content in argon fraction shows that the argon extraction rate of the air separation unit is low, and the potential of increasing production of the unit can be considered, so operations should be taken to increase argon production. Therefore, it is very important to detect the nitrogen content in the argon fraction to improve argon production in the air separation unit.

At present, most of the air separation units do not detect the nitrogen content in argon fraction online. A few devices for detecting nitrogen content in argon fraction comprise the special TCD or PDD analyzer for detecting. However, the special TCD or PDD analyzer can solve the problem of online detecting, the detecting period is too long (10 to 30 minutes), and the feedback data of nitrogen content is not in timely enough, which can not meet the requirements of online control.

SUMMARY

An object of the present disclosure is to provide a method, a device, and a storage medium for measuring nitrogen content, to adjust the detection result of the analyzer by soft-sensing method to realize the automatic online calibration, for preventing nitrogen blockage in the air separation unit.

The object of the present disclosure can be realized by the following technical proposal:

A method for measuring nitrogen content, comprises the following steps:
  determining related variables associated with the nitrogen content;
  establishing an initial model, wherein the initial model takes the related variables as independent variables and the nitrogen content as dependent variables according to a historical operation data, and calculating parameters in the initial model;
  according to parameters in the initial model, obtaining parameters in a soft-sensing model by fitting;
  according to detected values of the related variables and the soft-sensing model, predicting the nitrogen content in real-time; and
  according to the predicted nitrogen content and an actual nitrogen content obtained by periodic sampling, obtaining a fusion detection result.

A device for measuring nitrogen content, comprises a memory, a processor, and a program stored in the memory, wherein the processor implements the method as described above when executing the program.

A storage medium on which a program is stored that implements the method as described above when executed.

Compared with the conventional art, the present disclosure has the following beneficial effects:

(1) Low cost and convenient deployment: the fusion of the soft-sensing model and the analyzer detection result of the present disclosure is realized by a computer, without additional arrangement of equipment, and the soft-sensing technology only needs the existing data for modeling and calculation, so that the deployment is easy.

(2) Strong scalability: the soft-sensing model can adapt to different processes and variables and can be adjusted with the change of processes, so it has higher flexibility and scalability. In a case where the environment changes, the adaptation can be better realized by changing the expression form of the soft-sensing model.

(3) Higher timeliness: the soft-sensing model can predict the measurement result in real-time according to the actual operation data, and the response speed can reach in seconds, which can realize real-time online measurement.

(4) High detection accuracy: by combining the soft-sensing model and the analyzer, the present disclosure can utilize the characteristics of high timeliness of the soft-sensing model, overcome the defect of long detection time of the analyzer, and meet the requirement of online closed-loop control. Meanwhile, the soft-sensing model is periodically corrected with the detection result of the analyzer, so as to overcome the problem of precision decline caused by long-time error accumulation of the soft-sensing and improve the reliability of the detection result.

DETAILED DESCRIPTION OF THE EMBODIMENTS

The present disclosure will be described in detail below with reference to the accompanying drawings and specific embodiments. The embodiment is implemented on the premise of the technical proposal of the present disclosure, and the detailed implementation mode and the specific operation process are given, but the protection scope of the present disclosure is not limited to the following embodiments.

The present embodiment provides a method for measuring the nitrogen content, for predicting nitrogen content in argon fraction according to easily detectable variables having online data in the air separation unit, and obtaining the fusion detection result according to the predicted nitrogen content and the actual nitrogen content obtained by periodic sampling.

Figure 1:
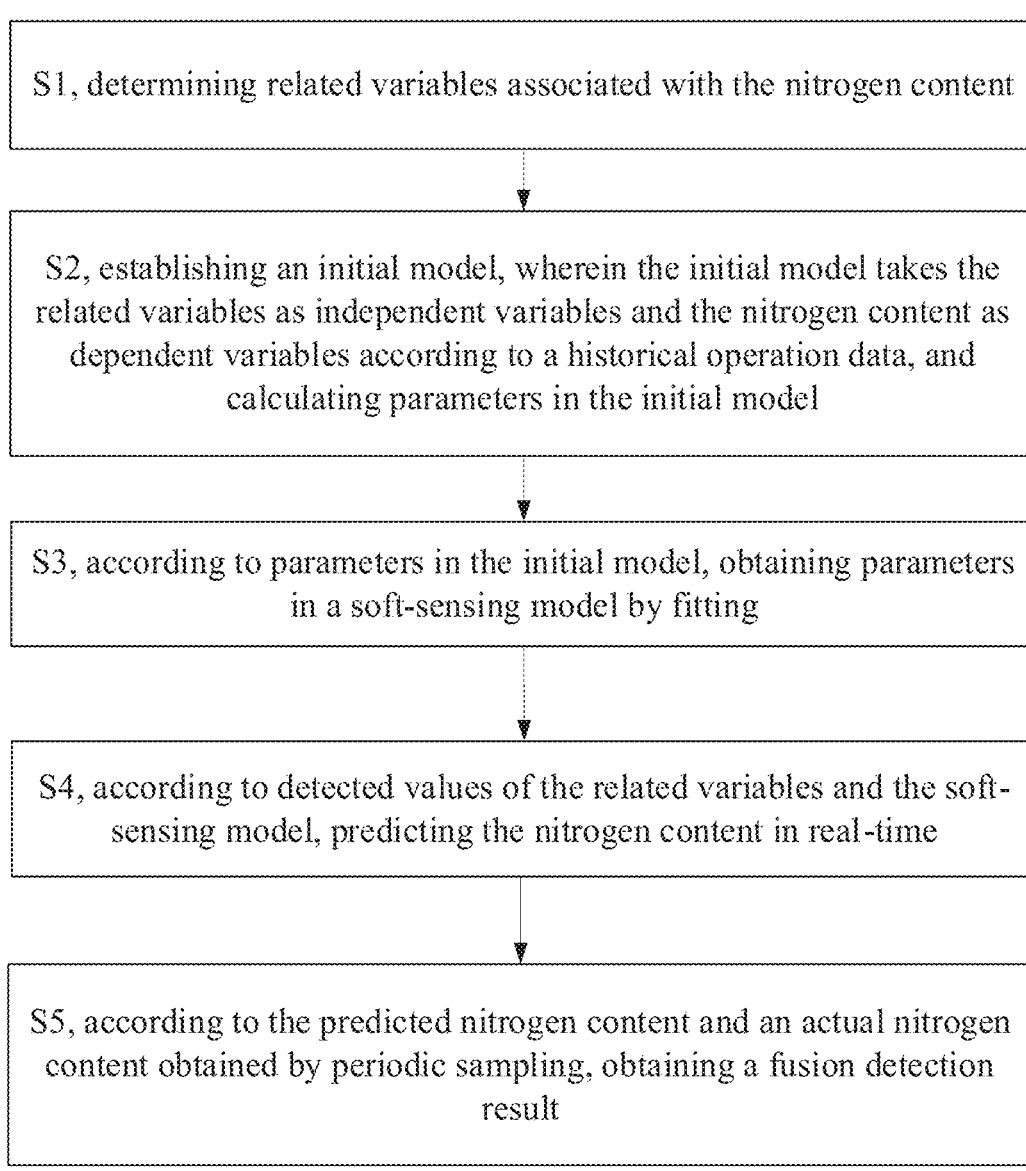
FIG. 1 is a flow chart of the method according to an embodiment of the present disclosure.

As shown in FIG. 1, the method comprises the following steps:

S1, determining related variables associated with the nitrogen content;

S2, establishing an initial model, wherein the initial model takes the related variables as independent variables and the nitrogen content as dependent variables according to a historical operation data, and calculating parameters in the initial model;

S3, according to parameters in the initial model, obtaining parameters in a soft-sensing model by fitting;

S4, according to detected values of the related variables and the soft-sensing model, predicting the nitrogen content in real-time; and S5, according to the predicted nitrogen content and an actual nitrogen content obtained by periodic sampling, obtaining a fusion detection result.

Optionally, S1: determining related variables associated with the nitrogen content in argon fraction.

The related variables can be selected from at least one of the: liquid void purity, argon fraction quantity, air quantity, argon fraction purity, upper column pressure, and argon fraction temperature. The detected values of the related variables can be easily detected by online measuring instruments. The process of air separation unit is complex and coupling is serious, so it is very important to select related variables reasonably for the soft-sensing. Choosing appropriate related variables can reduce the fitting difficulty of the soft-sensing and improve the measurement accuracy.

The related variables selected in the embodiment are shown in Table 1.

TABLE 1 related variables

| Number | Bit number | Related variable |
|---|---|---|
| 1 | AI001 | Liquid air purity |
| 2 | FI701 | Argon fraction quantity |
| 3 | FI101 | Air quantity |
| 4 | AI701 | Argon fraction purity |
| 5 | PI002 | Upper column pressure |
| 6 | TI701 | Argon fraction temperature |

Optionally, S2: establishing the initial model of the soft-sensing model of the nitrogen content in argon fraction, where the initial model takes the historical operation data of the related variables as independent variables and the historical operation data of the nitrogen content as dependent variables, and the soft-sensing model takes the detected data of the related variables as independent variables and predicted nitrogen content as dependent variables.

In the embodiment, the soft-sensing model is established employing multiple linear regression, and the model format is as follows:

$$\hat{y} = \beta_0 + \beta_1 x_1 + \beta_2 x_2 + \beta_3 x_3 + \beta_4 x_4 + \beta_5 x_5 + \beta_6 x_6$$

where $\hat{y}$ is the predicted nitrogen content by soft-sensing; $x_1 \sim x_6$ are the No. 1 to No. 6 related variables in Table 1 respectively; $\beta_0 \sim \beta_6$ are the parameters of the soft-sensing model. The related variables are six as an example in the embodiment and further can be one, two, three, or m related variables.

Optionally, S3: acquiring the parameters in the soft-sensing model with the historical operation data by fitting.

The historical operation data is sourced from at least one of the existing databases, real-time detection systems, simulations, or experiments. The soft-sensing needs a large amount of historical operation data to train the model, so it is necessary to collect the data related to the soft-sensing target. Data can be obtained from existing databases or real-time detection systems, and can also be generated through experiments or simulations. In order to ensure the accuracy and robustness of the soft-sensing model, it is required to obtain as much historical operation data as possible, especially the historical operation data under different working conditions.

For this purpose, the embodiment takes the following actions:

① Calibrate the instruments of all related variables in Table 1 to ensure the accuracy of detection;

② Adjust the operating conditions of the device; and

Because the variable load frequency of the air separation unit is relatively small, although some units have a long operating life, the operating conditions are relatively single, so it is impossible to have accumulated data with enough working conditions. Therefore, it is necessary to adjust the operating conditions of the device, comprising but not limited to: maximum oxygen production conditions, maximum liquid production conditions, minimum gas production conditions, minimum liquid production conditions, etc., so as to accumulate enough valuable actual data.

③ Read data from the real-time database.

In the embodiment, Microsoft Excel software is used to access the actual DCS real-time database online through OPC protocol, so as to obtain historical operation data.

In order to achieve the best fitting effect, before fitting parameters in the soft-sensing model with the historical operation data, the method further comprises processing the historical operation data to represent as:

$$y_i = \beta_{i0} + \beta_{i1} x_{i1} + \beta_{i2} x_{i2} + \beta_{i3} x_{i3} + \beta_{i4} x_{i4} + \beta_{i5} x_{i5} + \beta_{i6} x_{i6} + \varepsilon_i$$

The formula represents the variable relationship of the actual operation data obtained by each group in different conditions, for example, the n-th group of the historical operation data, where i=1, 2, 3 . . . n, n is the total number of historical operation data and $\varepsilon_i$ is a random error.

The n groups of the historical operation data can be expressed in matrix form as follows:

$$Y = C\beta + \varepsilon$$

where $$Y = [y_1 \; \cdots \; y_i \; \cdots \; y_n]^T$$

$$\beta = \begin{bmatrix} \beta_{10} & \beta_{11} & \beta_{12} & \beta_{13} & \beta_{14} & \beta_{15} & \beta_{16} \\ \vdots & \vdots & \vdots & \vdots & \vdots & \vdots & \vdots \\ \beta_{i0} & \beta_{i1} & \beta_{i2} & \beta_{i3} & \beta_{i4} & \beta_{i5} & \beta_{i6} \\ \vdots & \vdots & \vdots & \vdots & \vdots & \vdots & \vdots \\ \beta_{n0} & \beta_{n1} & \beta_{n2} & \beta_{n3} & \beta_{n4} & \beta_{n5} & \beta_{n6} \end{bmatrix}$$

-continued $$C = \begin{bmatrix} x_{10} & x_{11} & x_{12} & x_{13} & x_{14} & x_{15} & x_{16} \\ \vdots & \vdots & \vdots & \vdots & \vdots & \vdots & \vdots \\ x_{i0} & x_{i1} & x_{i2} & x_{i3} & x_{i4} & x_{i5} & x_{i6} \\ \vdots & \vdots & \vdots & \vdots & \vdots & \vdots & \vdots \\ x_{n0} & x_{n1} & x_{n2} & x_{n3} & x_{n4} & x_{n5} & x_{n6} \end{bmatrix}^T$$

$$\varepsilon = [\varepsilon_1 \ \ldots \ \varepsilon_i \ \ldots \ \varepsilon_n]^T.$$

The step of fitting parameters in the soft-sensing model with the historical operation data is employed with the least squares regression algorithm to obtain the following results:

$$\hat{\beta} = [C'C]^1 C^1 Y$$

$$\hat{\beta} = [\hat{\beta_0} \ \hat{\beta_1} \ \hat{\beta_2} \ \hat{\beta_3} \ \hat{\beta_4} \ \hat{\beta_5} \ \hat{\beta_6}]$$

The fitted soft-sensing model is as follows:

$$Y = \hat{\beta_0} + \hat{\beta_1} x_1 + \hat{\beta_2} x_2 + \hat{\beta_3} x_3 + \hat{\beta_4} x_4 + \hat{\beta_5} x_5 + \hat{\beta_6} x_6$$

According to $\hat{\beta}$, calculating the parameters of the soft-sensing model $\beta_0 \sim \beta_6$.

Compared with the online analyzer, the soft-sensing method has the following advantages:

1) Lower cost: Online analyzers need to purchase, install, maintain, and update equipment, while the soft-sensing technology can use existing process data for modeling and calculation, so the cost is lower.
2) Easy to deploy: Online analyzers need to be installed and debugged, while the soft-sensing technology only needs to use existing data for modeling and calculation, so it is easier to deploy.
3) Scalability: The soft-sensing technology can adapt to different processes and variables and can be adjusted with the change of processes, so it has higher flexibility and scalability.
4) Higher timeliness: The soft-sensing method can predict the detecting result in real-time according to the actual operation data, and the response speed can reach seconds.

Therefore, the embodiment adopts the mode of combining soft-sensing and analyzer, accelerates the sampling frequency of component detection, meets the requirement of online closed-loop control, and realizes real-time and reliable online detection while retaining higher detection accuracy, thereby providing reliable data sources for real-time online control of the air separation unit.

The detection result of the analyzer obtained by periodic sampling can periodically correct a fusion detection result.

The detection process of the analyzer is generally long, and the detection period of the analyzer adopted in the embodiment is 30 minutes. If only the analyzer is used, the demand for real-time online control cannot be met.

Optionally, S4: real-time acquiring values of the related variables associated with nitrogen content in argon fraction in the air separation unit to acquire a predicted nitrogen content based on the soft-sensing model; and Optionally, S5: according to the predicted nitrogen content based on the soft-sensing model, real-time adjusting the detection result of the analyzer to generate the fusion detection result of nitrogen content.

The embodiment uses the soft-sensing results with the analyzer results in a periodic correction mode. In the actual fusion process, it is hoped that the online analyzer can correct the fusion results after each detection, so an incremental algorithm is needed. Specifically:

$$AI1_K = j \cdot AI1_{K-1} + (1-j) \cdot AI1_b + \Delta AI1_{aK}$$

where $AI1_K$ is the fusion detection result at time K, $AI1_b$ is the actual nitrogen content, and $\Delta AI1_{aK}$ is the difference between the predicted nitrogen content at time K and the predicted nitrogen content at time K-1.

Further j={0,1}. In a case where time K is the sampling time for obtaining the actual nitrogen content, setting j=0, otherwise, setting j=1.

For example, when the analyzer completes sampling, setting j=0, and after the analyzer sampling and during each calculation period of soft-sensing, setting j=1.

Figure 2:
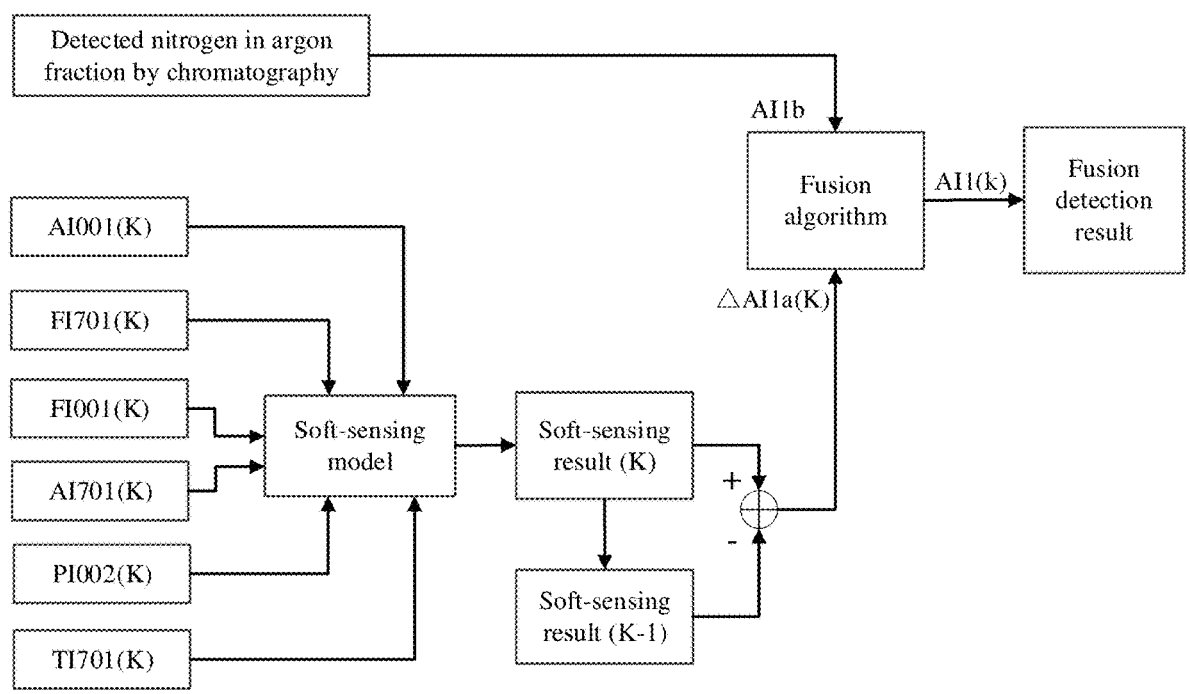
FIG. 2 is a flow chart illustrating the measuring process according to the embodiment of the present disclosure.

As shown in FIG. 2, the detected results of the analyzer are updated every half hour, that is, the actual nitrogen content is obtained by periodic sampling. When the detected results of the analyzer are updated and before calculating by soft-sensing, $$AI1_K = AI1_b + \Delta AI1_{aK}$$

That is, the fusion detection result at this time is based on the actual nitrogen content $AI1_b$.

After calculating by soft-sensing, for example, after one second, according to detected values of the related variables, predicting nitrogen content in real-time, and the fusion detection result is as follows:

$$AI1_K = AI1_{K-1} + \Delta AI1_{aK}$$

The fusion detection result is based on the fusion detection result $AI1_{K-1}$ at previous time and adjusted by the difference $\Delta AI1_{aK}$ between the two predicted nitrogen contents.

Therefore, during the half hour before the analyzer completes sampling and before the detected results is feedback, the nitrogen content can be continuously adjusted according to the soft-sensing model in every one second, and the real-time performance is strong.

Based on the above measurement methods, online commissioning and cross-verification are carried out.

Online Commissioning (1) Determining the process data collected in real-time: Before the soft-sensing model is put into use online, it is necessary to determine the process data collected in real-time for the real-time monitoring and control of the model; and
(2) Real-time monitoring and controlling: The soft-sensing model is applied to the process data collected in real-time for real-time monitoring and controlling. According to the output results of the soft-sensing model, the control decision is made.

Cross-Validation (1) Model verifying: The test set is applied to the soft-sensing model, and the error between the predicted results and the actual results is calculated to evaluate the generalization ability of the model; and (2) Evaluating the matching degree between the model and the actual. Generally, if the matching degree between the soft-sensing results and the actual detection results is above 95%, it will be considered usable, otherwise, the model needs to be modified, but it is also related to the requirements of the actual process for measurement accuracy, so it cannot be generalized.

Based on the above method, the equipment needed in the implementation process of the embodiment is shown in Table 2.

TABLE 2

Equipment required for implementation

| Number | Device name | Purpose |
|---|---|---|
| 1 | PDD or TCD chromatography | Determining of nitrogen content in argon fraction |
| 2 | Computer | Storing procedure data |
| 3 | Excel | Computational tools for regression modeling |

In one embodiment, the method is applied in a large air separation unit of a steel plant for online control. After being put into use, the probability of nitrogen blockage occurrence in the air separation unit is reduced from an average of 3 times/month to 1 time/month, which improves the stability and reliability of the operation of the unit. At the same time, the extraction rate of argon is increased by 3% (about 2 tons/day), and the economic benefit of the unit is increased by about 700,000/year.

When the air separation unit is equipped with an analyzer for nitrogen content in argon fraction, the present disclosure can accelerate the sampling frequency of component detection, greatly improve the detection speed, and meet the requirements of online closed-loop control by combining the soft-sensing with the online analyzer. At the same time, it reduces the problem of precision decline caused by long-term error accumulation of the soft-sensing, avoids the problem of frequent maintenance (ranging from several weeks to half a year), and improves the reliability of detection results. It can realize the online adjustment of nitrogen content in argon fraction, automatically optimize the operation conditions of the argon system in the air separation unit, improve the automation level of the unit, improve the operation stability of the unit, and improve the economic benefits of the unit.

In another embodiment, when there is no analyzer for detecting the nitrogen content of argon fraction in the device, the soft-sensing method in the present disclosure can be used as a reference to assist the operator in knowing the working condition in time, intervene in the working condition in advance, reduce the probability of nitrogen blockage in the argon system, and improve the argon production of the device.

The present disclosure is suitable for all air separation units with argon and has strong popularization and replicability. The present disclosure can be deployed separately or in the way of combining soft and hard circulation correction, which can improve the argon output of the air separation unit and have strong economic value.

In another embodiment, the improvement of the soft-sensing algorithm can be combined with more actual device operation parameters, so as to improve the accuracy of the soft-sensing and reduce the dependence on the analysis instrument, thereby further reducing the cost.

The above functions may be stored in a computer-readable storage medium if implemented in the form of software functional units and sold or used as separate products. Based on this understanding, the technical proposal of the present disclosure may be embodied in the form of a software product which is stored in a storage medium and comprises instructions for causing a computer device (which may be a personal computer, a server, a network device, etc.) to perform all or part of the steps of the method described in various embodiments of the present disclosure. The aforementioned storage media comprises a USB disk, a removable hard disk, a Read-Only Memory (ROM), a Random Access Memory (RAM), a magnetic disk or an optical disk, and other media capable of storing program codes.

Preferred embodiments of the present disclosure are described in detail above. It should be understood that several modifications and variations in accordance with the concepts of the present disclosure can be made without creative effort by those of ordinary skill in the art. Therefore, any technical solution that can be obtained by logical analysis, reasoning, or limited experiments based on the prior art according to the concept of the present disclosure by those skilled in the technical field should be within the scope of protection determined by the claims.

What is claimed is:

1. A method for measuring a nitrogen content, in an argon producing system to control the production of argon, wherein the argon producing system comprises an air separation unit for producing argon, an analyzer for obtaining an actual nitrogen content, and online measuring instruments for detecting related variables associated with the nitrogen content, wherein the related variables comprise at least one of liquid void purity, argon fraction quantity, air quantity, argon fraction purity, upper column pressure, and argon fraction temperature, wherein the method comprises the following steps:

determining the related variables associated with the nitrogen content;

establishing an initial model, by a processor, wherein the initial model takes the related variables as independent variables and the nitrogen content as dependent variables according to a historical operation data, and calculating parameters in the initial model, by the processor;

according to parameters in the initial model, obtaining parameters in a soft-sensing model by fitting, by the processor;

according to detected values of the related variables and the soft-sensing model, predicting the nitrogen content in real-time, by the processor, wherein the detected values of the related variables are detected by the online measuring instruments; and according to the predicted nitrogen content and the actual nitrogen content obtained through the analyzer by periodic sampling, obtaining, by the processor, a fusion detection result to be returned as a measured nitrogen content in an argon fraction of the air separation unit, so as to control argon production in the air separation unit based on the measured nitrogen content.

2. The method according to claim 1, wherein the step of, according to the predicted nitrogen content and the actual nitrogen content obtained by periodic sampling, obtaining the fusion detection result comprises:

calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;

wherein j={0,1}, in case where time K is a sampling time for obtaining the actual nitrogen content, setting j=0, otherwise, setting j=1.

3. The method according to claim 1, wherein the soft-sensing model is:

$$\hat{y} = \beta_0 + \beta_1 x_1 + \beta_2 x_2 + \beta_3 x_3 + \beta_4 x_4 + \beta_5 x_5 + \beta_6 x_6 \ldots + \beta_m x_m$$

wherein $\hat{y}$ is the predicted nitrogen content, $x_1 \sim x_m$ are the m related variables respectively, $\beta_0 \sim \beta_m$ are the soft-sensing model parameters.

4. The method according to claim 3, wherein the step of establishing the initial model comprises:
processing the historical operation data to be expressed as:

$$y_i = \beta_{i0} + \beta_{i1} x_{i1} + \beta_{i2} x_{i2} + \beta_{i3} x_{i3} + \beta_{i4} x_{i4} + \beta_{i5} x_{i5} + \beta_{i6} x_{i6} \ldots + \beta_{in} x_{in} + \varepsilon_i$$

for representing the variable relationship of the historical operation data obtained in n-th group, wherein i=1, 2, 3 . . . n, n is the total number group of historical operation data and $\varepsilon_i$ is a random error;
wherein n groups of the historical operation data are expressed in matrix form as follows:

$$Y = C\beta + \varepsilon$$

wherein $$\beta = \begin{bmatrix} \beta_{10} & \beta_{11} & \beta_{12} & \beta_{13} & \beta_{14} & \beta_{15} & \beta_{16} & \beta_{1m} \\ \vdots & \vdots & \vdots & \vdots & \vdots & \vdots & \vdots & \vdots \\ \beta_{i0} & \beta_{i1} & \beta_{i2} & \beta_{i3} & \beta_{i4} & \beta_{i5} & \beta_{i6} & \cdots & \beta_{im} \\ \vdots & \vdots & \vdots & \vdots & \vdots & \vdots & \vdots & \vdots \\ \beta_{n0} & \beta_{n1} & \beta_{n2} & \beta_{n3} & \beta_{n4} & \beta_{n5} & \beta_{n6} & \beta_{nm} \end{bmatrix}$$

$$C = \begin{bmatrix} x_{10} & x_{11} & x_{12} & x_{13} & x_{14} & x_{15} & x_{16} & x_{1m} \\ \vdots & \vdots & \vdots & \vdots & \vdots & \vdots & \vdots & \vdots \\ x_{i0} & x_{i1} & x_{i2} & x_{i3} & x_{i4} & x_{i5} & x_{i6} & \cdots & x_{im} \\ \vdots & \vdots & \vdots & \vdots & \vdots & \vdots & \vdots & \vdots \\ x_{n0} & x_{n1} & x_{n2} & x_{n3} & x_{n4} & x_{n5} & x_{n6} & x_{nm} \end{bmatrix}^T$$

$$\varepsilon = [\varepsilon_1 \ \ldots \ \varepsilon_i \ \ldots \ \varepsilon_n]^T.$$

5. The method according to claim 4, wherein the step of according to parameters of the initial model, obtaining soft-sensing model parameters by fitting, comprises:
obtaining with least squares regression algorithm:

$$\hat{\beta} = [C'C]^{-1} C^1 Y$$

$$\hat{\beta} = [\hat{\beta}_0 \ \hat{\beta}_1 \ \hat{\beta}_2 \ \hat{\beta}_3 \ \hat{\beta}_4 \ \hat{\beta}_5 \ \hat{\beta}_6 \ \ldots \ \hat{\beta}_m]$$

according to $\hat{\beta}$, calculating the parameters of the soft-sensing model $\beta_0 \sim \beta_m$.

6. The method according to claim 1, wherein the historical operation data is sourced from at least one of existing databases, real-time detection systems, simulations, or experiments.

7. The method according to claim 1, wherein the historical operation data is the data of the air separation unit running under a plurality of working conditions, and the working conditions comprise at least one of the maximum oxygen production condition, the maximum liquid production condition, the minimum gas production condition, and the minimum liquid production condition.

8. The method according to claim 3, wherein the step of, according to the predicted nitrogen content and the actual nitrogen content obtained by periodic sampling, obtaining the fusion detection result comprises:
calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;
wherein j={0,1}, in case where time K is a sampling time for obtaining the actual nitrogen content, setting j=0, otherwise, setting j=1.

9. The method according to claim 4, wherein the step of, according to the predicted nitrogen content and the actual nitrogen content obtained by periodic sampling, obtaining the fusion detection result comprises:
calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;
wherein j={0,1}, in case where time K is a sampling time for obtaining the actual nitrogen content, setting j=0, otherwise, setting j=1.

10. The method according to claim 5, wherein the step of, according to the predicted nitrogen content and the actual nitrogen content obtained by periodic sampling, obtaining the fusion detection result comprises:
calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;
wherein j={0,1}, in case where time K is a sampling time for obtaining the actual nitrogen content, setting j=0, otherwise, setting j=1.

11. The method according to claim 6, wherein the step of, according to the predicted nitrogen content and the actual nitrogen content obtained by periodic sampling, obtaining the fusion detection result comprises:
calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;

wherein j={0,1}, in case where time K is a sampling time for obtaining the actual nitrogen content, setting j=0, otherwise, setting j=1.

12. The method according to claim 7, wherein the step of, according to the predicted nitrogen content and the actual nitrogen content obtained by periodic sampling, obtaining the fusion detection result comprises:

calculating $$AI1_K = j \cdot AI1_{K-1} + (1-j) \cdot AI1_b + \Delta AI1_{aK}$$

wherein $AI1_K$ is the fusion detection result at time K, $AI1_b$ is the actual nitrogen content, and $\Delta AI1_{aK}$ is the difference between the predicted nitrogen content at time K and the predicted nitrogen content at time K-1;

wherein j={0,1}, in case where time K is a sampling time for obtaining the actual nitrogen content, setting j=0, otherwise, setting j=1.

13. The method according to claim 3, wherein the related variables comprise at least one of liquid void purity, argon fraction quantity, air quantity, argon fraction purity, upper column pressure, and argon fraction temperature.

14. The method according to claim 3, wherein the historical operation data is sourced from at least one of existing databases, real-time detection systems, simulations, or experiments.

15. The method according to claim 3, wherein the historical operation data is the data of the air separation unit running under a plurality of working conditions, and the working conditions comprise at least one of the maximum oxygen production condition, the maximum liquid production condition, the minimum gas production condition, and the minimum liquid production condition.

16. A system for measuring a nitrogen content to control the production of argon, comprising:

an air separation unit for producing argon;

an analyzer for obtaining an actual nitrogen content;

online measuring instruments for detecting related variables associated with the nitrogen content, wherein the related variables comprise at least one of liquid void purity, argon fraction quantity, air quantity, argon fraction purity, upper column pressure, and argon fraction temperature; and a device for measuring nitrogen content of the air separation unit, wherein the device comprises a memory, a processor, and a program stored in the memory, wherein when executing the program, the processor implements the method comprising the following steps:

determining the related variables associated with the nitrogen content;

establishing an initial model, by a processor, wherein the initial model takes the related variables as independent variables and the nitrogen content as dependent variables according to a historical operation data, and calculating parameters in the initial model, by the processor;

according to parameters in the initial model, obtaining parameters in a soft-sensing model by fitting, by the processor;

according to detected values of the related variables and the soft-sensing model, predicting the nitrogen content in real-time, by the processor, wherein the detected values of the related variables are detected by the online measuring instruments; and according to the predicted nitrogen content and the actual nitrogen content obtained through the analyzer by periodic sampling, obtaining, by the processor, a fusion detection result to be returned as a measured nitrogen content in an argon fraction of the air separation unit, so as to control the argon production in the air separation unit based on the measured nitrogen content.

* * * * *